United States Patent [19]

Steadman

[11] 4,087,301

[45] May 2, 1978

[54] METHOD OF FORMING A FLOW RESTRICTOR

[75] Inventor: Brian Lee Steadman, Alcester, England

[73] Assignee: Avon Medicals Limited, England

[21] Appl. No.: 714,117

[22] Filed: Aug. 13, 1976

[30] Foreign Application Priority Data

Aug. 22, 1975 United Kingdom .............. 34989/75

[51] Int. Cl.² ......................... B29C 17/00; F16K 7/06
[52] U.S. Cl. .................................. 156/198; 137/625.3; 138/40; 138/45; 138/115; 156/289; 156/290; 251/6
[58] Field of Search ..................... 251/4–10; 156/198, 289; 137/625.3; 138/40, 45 A, 115, 119

[56] References Cited

U.S. PATENT DOCUMENTS

| 3,624,800 | 11/1971 | Swick | 251/4 |
| 3,779,507 | 12/1973 | Clarke | 251/4 X |
| 3,802,463 | 4/1974 | Dabney | 251/6 X |

Primary Examiner—Martin P. Schwadron
Assistant Examiner—Richard Gerard
Attorney, Agent, or Firm—Watson, Leavenworth, Kelton & Taggart

[57] ABSTRACT

A flow restrictor is made by flattening a tube of flexible material about a member of cross-sectional characteristics representative of a desired flow passage, and securing the tube there, e.g. by rf welding. The member is then removed leaving a determinate flow passage in which problems of creep do not arise. The restrictor may have parallel to the flow passage a portion of the tube which is not permanently secured together so as to leave a by-pass which can be open to give a comparatively unrestricted flow passage or can be temporarily completely closed by external compression. A single tube may have in line a plurality of such restrictors with by-passes, the flow passages of the various restrictors being of different flow characteristics. The flow characteristic required is obtained by closing off the by-pass associated with the selected flow passage.

6 Claims, 9 Drawing Figures

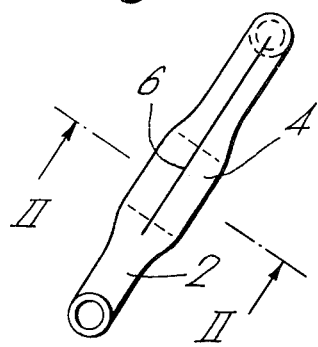
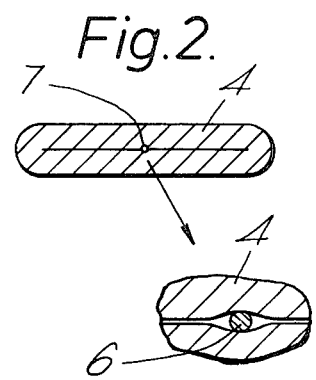
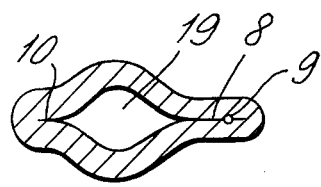
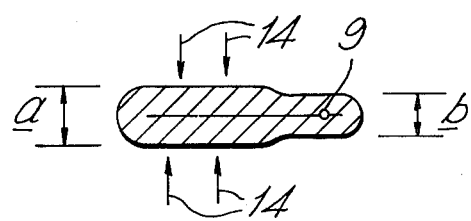
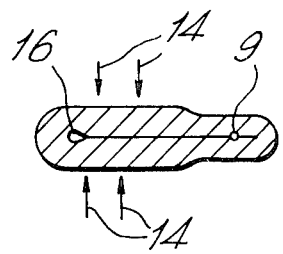

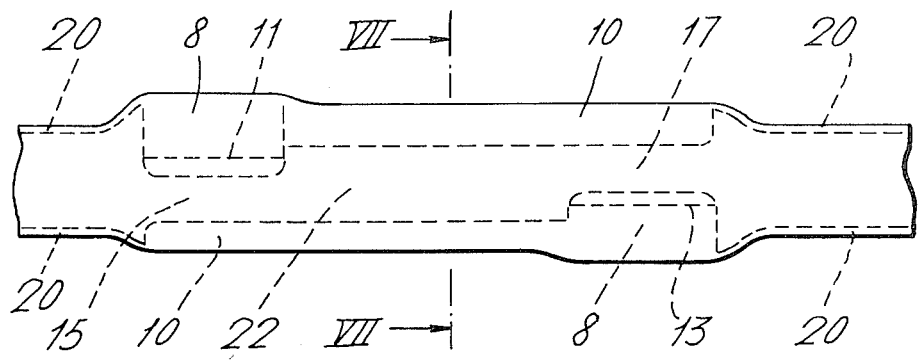
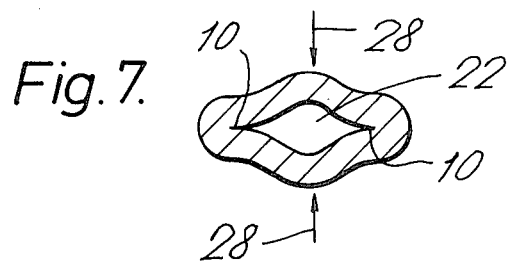
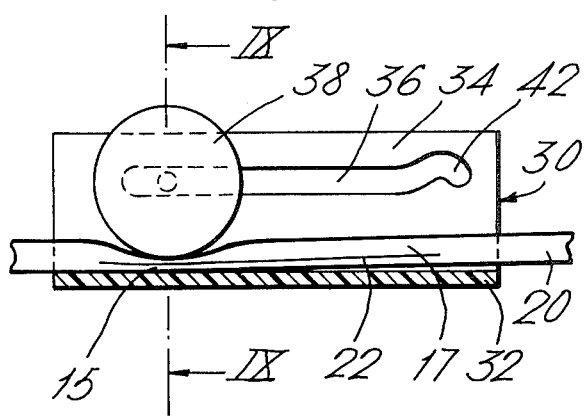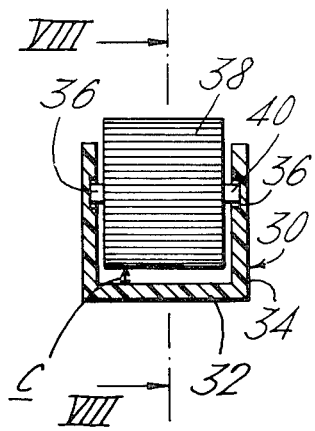

METHOD OF FORMING A FLOW RESTRICTOR

FIELD OF THE INVENTION

This invention relates to flow restrictors. These flow restrictors may be used in medical intravenous administration sets but are not limited to such use.

BACKGROUND OF THE INVENTION

Such administration sets customarily include a length of plastics tubing, frequently p.v.c. and rely upon compression of this tubing by a clamp to control the rate of flow. The degree or position of compression is variable to vary the rate of flow and a problem is that "creep", i.e., cold flow of the plastics material after setting of the clamp, leads to alteration in the passage through the clamped section of tubing.

Various solutions have been proposed to this problem, as for example in United Kingdom Patent Specifications Nos. 1,319,090 (Adelberg) and 1,361,405 (Clarke).

SUMMARY OF THE INVENTION

This invention seeks to provide an alternative solution to the problem and one which is of relative simplicity, since the flow passage is formed in an essentially solid block of material of the tube so that it has permanently defined characteristics. Of course, that narrow flow passages such as capillaries as a general proposition can exist and will affect flow through them is known, but the present invention is concerned with methods of making such passages from comparatively large bore flexible tube, in a simple manner and with a high degree of accuracy. The method allows also for the formation of a comparatively wide bypass aperture parallel to the flow passage but within the same flexible tube.

According to this invention there is provided a method of forming a flow restrictor which consists of positioning a thin, elongate member within a flexible tube, flattening the tube about the member to bring internal wall surfaces of the tube into contact with each other at each lateral side of the member, permanently securing the contacting wall surfaces to each other and removing the member to leave a flow passaage of a cross-section defined by that of the member.

Preferably the said portions are so secured across only a portion of the tube whereby a flexible further passage is left within the tube to act as a bypass. The bypass has a cross sectional area greater than that of the flow passage but less than the cross section of the flexible tube. Then, a clamp may be applied to the wall portions defining the further passage whereby it (but not the flow passage) may be closed to fluid flow.

The securing of the wall portions to each other is preferably by bonding by welding, especially by rf welding, and is preferably such that any interface between the face portions disappears.

The member, particularly when the tube is of p.v.c. may be a nylon filament.

The invention comprises also a flow restrictor made by the said method.

The restrictor may comprise a plurality of the said flow passages and bypasses in axially spaced relationship, the flow passages having respectively different fluid passing characteristics.

If the deformation and sealing of the first length of tubing around the hollow member does not extend across the full transverse width of the first tube it is then preferred that the portion which defines the further passage is permanently deformed to a shape which can be closed without the applicaton of such clamping pressure that there is risk of closing the flow passage. A clamp which cannot exert such pressure may be provided.

DESCRIPTION OF THE DRAWINGS

Embodiments of the invention will be described by way of example with reference to the accompanying drawings:

FIG. 1 is a perspective view of a flow restrictor;

FIG. 2 is an enlarged cross section on the line II—II of FIG. 1;

FIGS. 3 and 4 are a similar cross section of a different flow restrictor in its open and restricted conditions;

FIG. 5 is an analogous cross section to FIG. 4 illustrating a less preferably modification;

FIG. 6 is an enlarged plan view of a double restrictor;

FIG. 7 is an enlarged cross section on the line VII—VII of FIG. 6,

FIGS. 8 and 9 are two sections on the lines IX—IX and VIII—VIII respectively through a roller clamp for use in conjunction with the double restrictor of FIG. 6, the restrictor being shown in FIG. 8, but not in FIG. 9.

DESCRIPTION OF PREFERRED EMBODIMENTS

Referring firstly to FIG. 1 and 2 of the drawings the flow restrictor consists of a first length 2 of flexible tubing in this example pvc tubing of 5 mm internal diameter. In this embodiment the whole of the internal surface of the wall of the tubing has been brought together along a length 4 by flattening it face to face with the interposition between it of a narrow member 6, here a nylon monofilament. The length 4 has been deformed and sealed around the member 6 at each of its lateral sides by means of an rf weld between the hammer and anvil of any commercially available welding machine. Heat sealing would be an alternative way of sealing the length 4 around the member 6. The welding or other securing will preferably be carried out so as to eliminate any interface between the internal face regions of the tube being secured together. At least one end of the member 6 is left axially projecting from the secured length 4. After the welding or other securing is complete, the member 6 is removed by being pulled along the tube. As seen from FIG. 2 the member 6 will leave a very narrow gap 7 through the length 4 which will serve as a flow passage to govern the rate of flow of fluid through the first tube 2, in dependence on many factors (apart from the viscosity or head of the fluid) such as the diameter or shape of the member 6, and the axial length over which the wall is flattened and secured. However, each flow passage 7 has a fixed and individual flow rate which cannot be varied once it has been manufactured. It is set into what is essentially a solid block of the material of the tube.

A range of such restrictors could be made, using various sizes of member 6 to give predetermined flow rates at given values of hydrostatic head and viscosity of fluid to be administered. Such restrictors could be incorporated by the user, e.g. hospital staff, at any point of their choice in any device involving the delivery of fluid through tubes. For example, such a restrictor could conveniently be incorporated into the outlet end of an administration set where it connects with the needle or cannula. If the restrictor were to be fitted there the set could be primed before use in an unrestricted condition (easier than priming it in a restricted condition) and then connected to the restrictor.

A restrictor could be permanently fitted into an administration set at various points. However, it could then be difficult to fill the section of the set downstream of the restrictor during priming. To overcome this it is preferable to employ a restrictor with a cross section as illustrated by FIGS. 3 and 4 which is at present the most preferred embodiment of restrictor. This restrictor is also formed from a first length of p.v.c. tubing. During formation, however, the member 6 is placed to one side of the tube 2 and rf weld is performed over it at one side of the tube extending over only a part of the total internal wall of the tube, the interface of the welding being indicated for simplicity in FIG. 3 by reference number 8 (although in actually carrying out the process the interface would preferably disappear). A small second weld 10 is applied at the opposite side of the tube giving that side of the tube the slightly pinched shape seen in FIG. 3. The aperture 19 defined by the unwelded wall portion of the tube forms a by-pass around the flow passage 9 left by the removal of member 6.

In use the set is primed with the restrictor in the condition illustrated in FIG. 3, and there is relatively free flow through the by-pass aperture 19 for priming. Once the set has been primed clamping pressure is applied across the by-pass aperture 19 to close it to the condition shown in FIG. 4, the clamping pressure being denoted by the arrows 14. The clamping pressure closes the opening 19 completely; once it has been applied only the restricted flow through the flow passage 9 is possible.

The purpose of the weld 10 is to facilitate closing the by-pass aperture 19. If the weld were not present, the application of the same clamping pressure would compress the tubing to the cross section shown in FIG. 5, with a small residual opening remaining at 16. This would close slowly over an extended period of time through "creep" i.e., cold flow of the plastics material.

The residual opening 16 might be effectively closed by the application of very much heavier clamping pressure. However, this would then carry the risk of constricting the flow passage. Accordingly, it is preferable to provide the rf weld 10. Preferably also the total wall thickness (in the direction of application of the clamping pressure) is greater in the region of the aperture 19 (dimemsion a in FIG. 4), than in the region of the flow passage 9, (dimension b) as a result of the securing operation carried out in that region so that when clamping pressure sufficient only to close the aperture 19 is applied, no pressure is applied to the region around the flow passage 9. A clamping device will preferably be used which is incapable of applying a pressure so excessive that there is compression in that latter region.

A double restrictor is shown in plan view at FIG. 6. This restrictor is again formed from a length of p.v.c. tubing whose walls are indicated at 20. Two axially spaced-apart flow passages 11 and 13 are provided. These are of different characteristics but both are formed by rf welds 8 analogously with the restrictor illustrated by FIG. 3. As with that restrictor, opposite the rf welds 8 which sealed around the members 11 and 13 there are provided small rf welds 10. There are by-pass apertures 15, 17 analogous to the by-pass 19. The cross sections in the regions of the welds 8 are therefore almost identical to the cross section illustrated at FIG. 3. The small rf welds 10 overlap in the central region so that the cross section on the line VII—VII is as shown by FIG. 7. There is an aperture 22 between them. Such a restrictor can be incorporated into an administration set and for priming the set no clamping pressure is applied at any point so that liquid can flow through the passageway 17, 22, 15. To stop flow completely clamping pressure can be applied approximately on the line VII—VII and as illlustrated by the arrows 28 in FIG. 7, to close the aperture 22 completely. To obtain restricted flow clamping pressure is applied to one of the by-pass apertures 15 or 17 to close it and limit the flow to that passing through corresponding flow passage 11 or 13. Since passages 11 and 13 are of different sizes different flows will be selected by clamping either the by-pass 15, or the by-pass 17.

Clamping pressure may be applied by means of a roller clamp as illustrated by FIGS. 8 and 9. The clamp has a generally channel section body 30 with a floor 32 and side walls 34, the latter having two longitudinal grooves 36. A roller 38 has two stub axles 40 which locate in these grooves. The tube of the administration set runs along the body 30 with the double restrictor between the roller 38 and the floor 32. The gap c between the roller 38 and the floor 32 is very slightly less than dimension a, i.e., twice the wall thickness of the double restrictor in the region of any of the apertures 22, 15 or 17. As shown in FIG. 8 the restrictor is placed in the clamp so that when the roller is at different points along the track it will bear on one or other of the by-pass apertures 15 or 17 or the central aperture 22. At one end 42, the track rises away from the floor 32 to provide a resting point for the roller 38 which will keep it from clamping the double restrictor to allow free flow through the aperture 22, 15 and 17 for priming the administration set, or during shipment and storage of the set before use.

I claim:

1. A method of forming a flow restrictor which comprises positioning a thin, elongate member within a flexible tube, flattening the tube about the member to bring internal wall surfaces of the tube into contact with each other at each lateral side of the member, permanently securing the contacting wall surfaces to each other at each lateral side of the member but over only a part of the area of the internal wall surface of the tube on at least one lateral side of the member and removing the member to leave a flow passage of a cross-section defined by that of the member, and the unsecured part of the internal wall surface of the tube defining a bypass in parallel with the flow passage.

2. A method as claimed in claim 1 wherein the tube is of pvc and the member is a nylon filament.

3. A method as claimed in claim 1 comprising placing a plurality of said members of different cross sectional characteristics spaced apart in the longitudinal direction of the tube and securing respective portions of internal wall surface of the tube around the respective members whereby to provide, after the removal of the members, a restrictor having a plurality of flow passages of different characteristics respectively selectable to be effective by closing off the respectively associated bypass.

4. A method as claimed in claim 1 comprising permanently deforming the wall portion defining the bypass such that a pressure sufficient to close the bypass is lowered to a value at which the flow passage is unaffected.

5. A method as claimed in claim 4 comprising deforming the said bypass by pinching together and permanently securing together internal wall surfaces of the tube laterally most remote from the member.

6. A method as claimed in claim 1 which includes securing the wall surfaces together under a pressure sufficient to lessen permanently the total thickness of the walls secured together, so that the thickness of the walls over an area extending from one lateral side of the flow passage to the other is less than the total thickness of the walls defining the bypass whereby clamping compression applied to the bypass to close it does not affect the said area of wall.

* * * * *